(12) United States Patent
Heidelbaugh et al.

(10) Patent No.: US 8,119,807 B2
(45) Date of Patent: Feb. 21, 2012

(54) QUINOLYNYLMETHYLIMIDIZOLES AS THERAPEUTIC AGENTS

(75) Inventors: Todd M. Heidelbaugh, Fountain Valley, CA (US); Phong X. Nguyen, Placentia, CA (US); Ken Chow, Newport Coast, CA (US); Michael E. Garst, Newport Beach, CA (US)

(73) Assignee: Allergan, Inc., Irvine, CA (US)

( * ) Notice: Subject to any disclaimer, the term of this patent is extended or adjusted under 35 U.S.C. 154(b) by 386 days.

(21) Appl. No.: 12/522,878

(22) PCT Filed: Jan. 4, 2008

(86) PCT No.: PCT/US2008/050158
§ 371 (c)(1),
(2), (4) Date: Jul. 10, 2009

(87) PCT Pub. No.: WO2008/088937
PCT Pub. Date: Jul. 24, 2008

(65) Prior Publication Data
US 2010/0076020 A1    Mar. 25, 2010

Related U.S. Application Data

(60) Provisional application No. 60/884,708, filed on Jan. 12, 2007, provisional application No. 60/917,797, filed on May 14, 2007.

(51) Int. Cl.
*C07D 215/38* (2006.01)
(52) U.S. Cl. .................................................. 546/159
(58) Field of Classification Search .............. 546/159; 514/312
See application file for complete search history.

(56) References Cited

U.S. PATENT DOCUMENTS

| | | | |
|---|---|---|---|
| 4,814,343 A | 3/1989 | Cossement | |
| 5,151,526 A | 9/1992 | Hsu et al. | |
| 6,329,369 B1 | 12/2001 | Chow et al. | |
| 6,465,486 B1 | 10/2002 | Baxter | |
| 6,841,684 B2 | 1/2005 | Chow et al. | |
| 7,868,020 B2 * | 1/2011 | Heidelbaugh et al. | 514/311 |
| 8,013,169 B2 * | 9/2011 | Heidelbaugh et al. | 548/346.1 |
| 2002/0019390 A1 | 2/2002 | Wong et al. | |
| 2003/0023098 A1 | 1/2003 | Chow et al. | |
| 2006/0069144 A1 | 3/2006 | Heidelbaugh | |

FOREIGN PATENT DOCUMENTS

| | | |
|---|---|---|
| EP | 0 024 829 | 8/1980 |
| EP | 1 413 576 | 12/1998 |
| WO | WO 98/46572 | 10/1998 |
| WO | WO 99/28300 | 6/1999 |
| WO | WO 01/00586 | 1/2001 |
| WO | WO 02/076950 | 10/2002 |
| WO | WO 2006/036497 | 4/2006 |
| WO | WO 2006/036507 | 4/2006 |

OTHER PUBLICATIONS

Prezeslawski R., et al.; "Synthesis and Alpha2-Adrenergic Activity of Quinoline and Quinoxaline Analogues of Medetomidine"; Proceedings of the Erdec Scientific Conference on Defense Research; Nov. 1994; pp. 121-127; XP008091151.
Seoung-Soo Hong et al; "A Structure-Activity Relationship Study of Benzylic Modifications of 441-(I-Naphthyl)ethyl]-1H-imidazoleos n al- and az-Adrenergic Receptors"; J. Med. Chem. 1994,37, 2328-2333.
Shilpa G. Lalchandani, et al; "Medetomidine analogs as selective agonists for the human a2-adrenoceptors"; Biochemical Pharmacology 67 (2004) 87-96.
D.D Miller, et al.; "Synthesis and biological Activity of a Series of Comformationally Restricted Analogs of 4-Substituted Imidazoles as $a_2$-Adrenergic Agonists"; Proceedings of the Erdec Scientific Conference on Defense Research; Nov. 1994; pp. 113-119.
Yoshiya Amemiya et al.; "Medetomidine Analogs as $a_2$-Adrenergic Agonists"; Egypt J. Pharm. Sci. 35, No. 1-6, pp. 403-410; 1994.
Yoshiya Amemiya et al.; "Synthesis and a-AdrenergicActivvities of 2- and 4-Substituted Imidazoline and Imidazole Analogues of α and β-Naphthalene"; Egypt J. Pharm. Sci. 35, No. 1-6, pp. 91-112; 1994.
B. V. Venkataraman el at.; "Structure-Activity Studies of New Imidazolines on Adrenoceptors of Rat Aorta and Puman Platelets"; Naunyn-Schmiedeberg's Arch Pharma, 344:454-463; 1994.

* cited by examiner

*Primary Examiner* — D M Seaman
(74) *Attorney, Agent, or Firm* — Doina G. Ene; John E. Wurst; Kevin J. Forrestal

(57) ABSTRACT

Disclosed herein is a compound of the formula (I): (I). Therapeutic methods, compositions and medicaments related thereto are also disclosed.

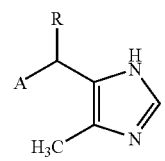

(1)

12 Claims, No Drawings

QUINOLYNYLMETHYLIMIDIZOLES AS THERAPEUTIC AGENTS

CROSS REFERENCE TO RELATED APPLICATIONS

This is a national stage application under 35 U.S.C. §371 of PCT patent application PCT/US08/50158, filed on Jan. 4, 2008, which claims the benefit of U.S. Provisional Patent Application 60/884,708, filed Jan. 12, 2007 and U.S. Provisional Application Ser. No. 60/917,797, filed May 14, 2007, each of which is hereby incorporated by reference in its entirety.

DESCRIPTION OF THE INVENTION

Disclosed herein is a compound of the formula

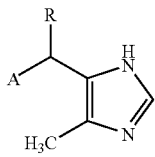

wherein R is H, $C_{1-4}$ alkyl, or $CF_3$;
A is quinolinyl having 0, 1, 2, or 3 stable substituents consisting of from 1 to 8 heavy atoms and any required hydrogen atoms, said heavy atoms being selected from C, N, O, S, F, Cl, Br, I, and any combination thereof.

Another embodiment is a method comprising administering a compound disclosed herein to a patient in need thereof for the treatment of glaucoma or ocular hypertension.

DEFINITIONS, EXPLANATIONS, AND EXAMPLES

Unless explicitly and unambiguously indicated otherwise, the definitions, explanations, and examples provided in this section shall be used to determine the meaning of a particular term or expression where there is any ambiguity arising from other parts of this document or from any disclosure incorporated by reference herein.

Hydrocarbyl is a moiety consisting of carbon and hydrogen, including, but not limited to:

1. alkyl, which is hydrocarbyl containing no double or triple carbon-carbon bonds; alkyl includes, but is not limited to:
   linear alkyl, cyclic alkyl, branched alkyl, and combinations thereof;
   $C_{1-4}$ alkyl, which refers to alkyl having 1, 2, 3, or 4 carbon atoms, including, but no limited to, methyl, ethyl, isopropyl, cyclopropyl, n-propyl, n-butyl and the like;
   $C_{1-6}$ alkyl, which refers to alkyl having 1, 2, 3, 4, 5, or 6 carbon atoms; including, but not limited to methyl, ethyl, propyl isomers, cyclopropyl, butyl isomers, cyclobutyl, pentyl isomers, cyclopentyl, hexyl isomers, cyclohexyl, and the like;
   combinations of these terms are possible, and their meanings should be obvious to those of ordinary skill in the art; for example $Cl_{1-6}$ linear alkyl would refer to $C_{1-6}$ alkyl which is also linear;
2. alkenyl, which is hydrocarbyl containing one or more carbon-carbon double bonds; alkenyl includes, but is not limited to:
   linear alkenyl, cyclic alkenyl, branched alkenyl, and combinations thereof;
   alkenyl having 1, 2, 3, or more carbon-carbon double bonds;
3. alkynyl, which is hydrocarbyl containing one or more carbon-carbon triple bonds; akynyl includes, but is not limited to:
   linear alkynyl, cyclic alkynyl, branched alkynyl, and combinations thereof;
   alkynyl having 1, 2, 3, or more carbon-carbon double bonds;
4. aryl, provided that it contains no heteroatoms either in a ring or as a substituent;
5. combinations of any of the above;
6. $C_{1-4}$ hydrocarbyl, which refers to hydrocarbyl having 1, 2, 3, or 4 carbon atoms; and
7. $C_{1-6}$ hydrocarbyl, which refers to hydrocarbyl having 1, 2, 3, 4, 5, or 6 carbon atoms.

Alkoxy is O-alkyl, such as $OCH_3$, O-ethyl, O-isopropyl, and the like.

Mercaptoakyl is S-alkyl, such as SCH3, S-ethyl, S-isopropyl, and the like

Acyloxy is

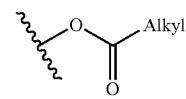

A compound, substituent, moiety, or any structural feature is stable if it is sufficiently stable for the compound to be isolated for at least 12 hours at room temperature under normal atmospheric conditions, or if it is sufficiently stable to be useful for at least one use disclosed herein.

A heavy atom is an atom which is not hydrogen.

A heteroatom is an atom which is not carbon or hydrogen.

A pharmaceutically acceptable salt is any salt that retains the activity of the parent compound and does not impart any additional deleterious or untoward effects on the subject to which it is administered and in the context in which it is administered compared to the parent compound. A pharmaceutically acceptable salt also refers to any salt which may form in vivo as a result of administration of an acid or another salt.

Pharmaceutically acceptable salts of acidic functional groups may be derived from organic or inorganic bases. The salt may comprise a mono or polyvalent ion. Of particular interest are the inorganic ions lithium, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Hydrochloric acid or some other pharmaceutically acceptable acid may form a salt with a compound that includes a basic group, such as an amine or a pyridine ring.

Unless otherwise indicated, reference to a compound should be construed broadly to include pharmaceutically acceptable salts, and tautomers of the depicted structure. For example, the structures herein are intended to include, but are not limited to, the tautomeric forms shown below.

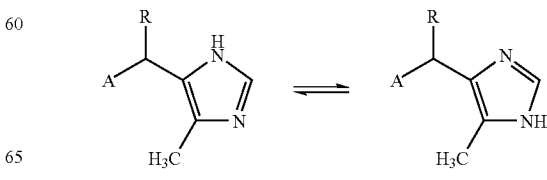

Unless stereochemistry is explicitly depicted, a structure is intended to include every possible stereoisomer, both pure or in any possible mixture.

For the purposes of this disclosure, "treat," "treating," or "treatment" refer to the use of a compound, composition, therapeutically active agent, or drug in the diagnosis, cure, mitigation, treatment, prevention of disease or other undesirable condition, or to affect the structure or any function of the body of man or other animals.

R is H, $C_{1-4}$ alkyl, or $CF_3$. Thus, the following compounds are contemplated.

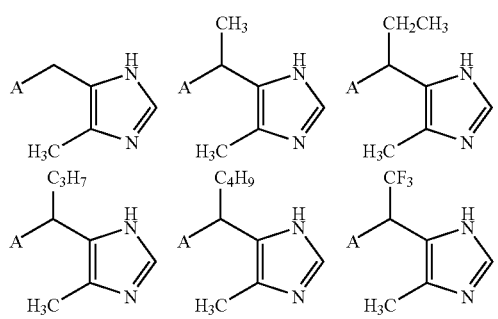

In one embodiment R is H.

A is quinolinyl having 0, 1, 2, or 3 stable substituents consisting of from 1 to 8 heavy atoms and any required hydrogen atoms, said heavy atoms being selected from C, N, O, S, F, Cl, Br, I, and any combination thereof.

Quinolinyl is one of the moieties below

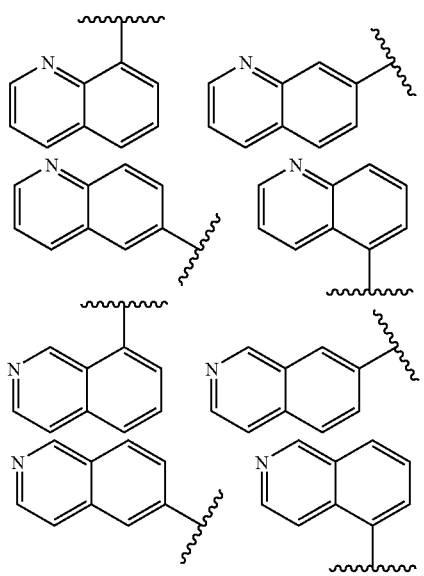

which may have substituents according to the parameters set forth herein.

Thus, for example, A may be any of the structures shown below or the like, wherein $R^1$, $R^2$, and $R^3$ are independently hydrogen or stable substituents consisting of from 1 to 8 heavy atoms and any required hydrogen atoms, said heavy atoms being selected from C, N, O, S, F, Cl, Br, I, and any combination thereof; and n is 0, 1, 2, or 3.

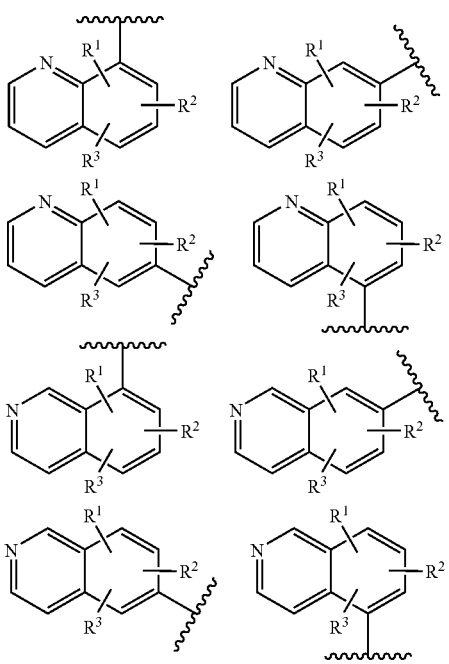

The position of $R^1$, $R^2$, and $R^3$ may be anywhere on the ring system, and are not limited to the particular ring where they are located in the structural depiction.

While not intending to be limiting, examples of stable substituents consisting of from 1 to 8 heavy atoms and any required hydrogen atoms include:

hydrocarbyl, including alkyl, such as methyl, ethyl, propyl isomers, butyl isomers, and the like; alkenyl, alkynyl, and phenyl;

alkoxy, mercaptoalkyl, acyloxy, amino, including $NH_2$, NH-alkyl, N(alkyl)$_2$, where the alkyl groups are the same or different;

halo, including F, Cl, Br, and I; and $CH_2CN$, CN; $NO_2$; OH.

If a substituent is a salt, for example of a carboxylic acid or an amine, the counterion of said salt, i.e. the ion that is not covalently bonded to the remainder of the molecule is not counted for the purposes of the number of heavy atoms in a substituent. Thus, for example, the salt —$CO_2^-Na^+$ is a stable substituent consisting of 3 heavy atoms, i.e. sodium is not counted. In another example, the salt —$NH(Me)_2^+Cl^-$ is a stable substituent consisting of 3 heavy atoms, i.e. chlorine is not counted.

In one embodiment, the substituents selected from are methyl, ethyl, propyl isomers, F, Cl, Br, I, $OCH_3$, $NH_2$, $N(CH_3)_2$, and combinations thereof.

In another embodiment substituents are selected from $CH_3$, ethyl, t-butyl, ethenyl, ethynyl, $OCH_3$, NHMe, $NMe_2$, Br, Cl, F, phenyl, and combinations thereof.

In another embodiment A is unsubstituted.

Another embodiment is a compound having the formula

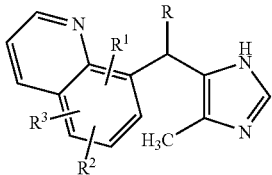

wherein $R^1$, $R^2$, and $R^3$ are independently hydrogen or stable substituents consisting of from 1 to 8 heavy atoms and any required hydrogen atoms, said heavy atoms being selected from C, N, O, S, F, Cl, Br, I, and any combination thereof; and n is 0, 1, 2, or 3.

Another embodiment is a compound having the formula

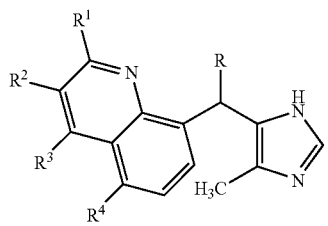

wherein $R^1$, $R^2$, $R^3$, and $R^4$ are independently hydrogen or stable substituents consisting of from 1 to 8 heavy atoms and any required hydrogen atoms, said heavy atoms being selected from C, N, O, S, F, Cl, Br, I, and any combination thereof; and n is 0, 1, 2, or 3.

Another embodiment is a compound having the formula

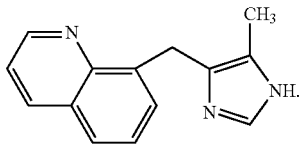

Another embodiment is a compound having the formula

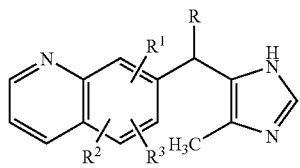

wherein $R^1$, $R^2$, and $R^3$ are independently hydrogen or stable substituents consisting of from 1 to 8 heavy atoms and any required hydrogen atoms, said heavy atoms being selected from C, N, O, S, F, Cl, Br, I, and any combination thereof; and n is 0, 1, 2, or 3.

Another embodiment is a compound having the formula

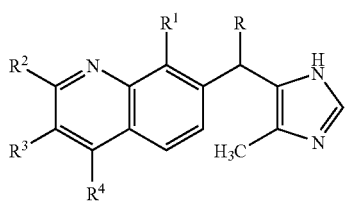

wherein $R^1$, $R^2$, $R^3$, and $R^4$ are independently hydrogen or stable substituents consisting of from 1 to 8 heavy atoms and any required hydrogen atoms, said heavy atoms being selected from C, N, O, S, F, Cl, Br, I, and any combination thereof; and n is 0, 1, 2, or 3.

Another embodiment is a compound having the formula

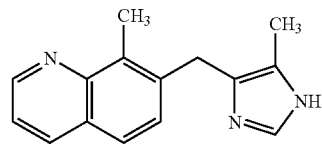

Another embodiment is a compound having the formula

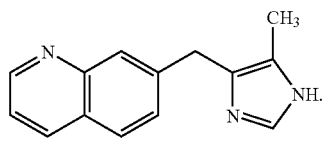

Biological Data

Receptor Selection and Amplification Technology (RSAT) Assay

The RSAT assay measures a receptor-mediated loss of contact inhibition that results in selective proliferation of receptor-containing cells in a mixed population of confluent cells. The increase in cell number is assessed with an appropriate transfected marker gene such as □-galactosidase, the activity of which can be easily measured in a 96-well format. Receptors that activate the G protein, Gq, elicit this response. Alpha2 receptors, which normally couple to Gi, activate the RSAT response when coexpressed with a hybrid Gq protein that has a Gi receptor recognition domain, called Gq/i5.

NIH-3T3 cells are plated at a density of 2×106 cells in 15 cm dishes and maintained in Dulbecco's modified Eagle's medium supplemented with 10% calf serum. One day later, cells are cotransfected by calcium phosphate precipitation with mammalian expression plasmids encoding p-SV-β-galactosidase (5-10 μg), receptor (1-2 μg) and G protein (1-2 μg). 40 μg salmon sperm DNA may also be included in the transfection mixture. Fresh media is added on the following day and 1-2 days later, cells are harvested and frozen in 50 assay aliquots. Cells are thawed and 100 μl added to 100 μl aliquots of various concentrations of drugs in triplicate in 96-well dishes. Incubations continue 72-96 hr at 37° C. After washing with phosphate-buffered saline, β-galactosidase enzyme activity is to determined by adding 200 μl of the chromogenic substrate (consisting of 3.5 mM o-nitrophenyl-β-D-galactopyranoside and 0.5% nonidet P-40 in phosphate buffered saline), incubating overnight at 30° C. and measuring optical density at 420 nm. The absorbance is a measure of enzyme activity, which depends on cell number and reflects a receptor-mediated cell proliferation. The efficacy or intrinsic activity is calculated as a ratio of the maximal effect of the drug to the maximal effect of a standard full agonist for each receptor subtype. Brimonidine, also called UK14304, the chemical structure of which is shown below, is used as the standard agonist for the alpha$_{2A}$, alpha$_{2B}$ and alpha$_{2C}$ receptors. The EC$_{50}$ is the concentration at which the drug effect is half of its maximal effect.

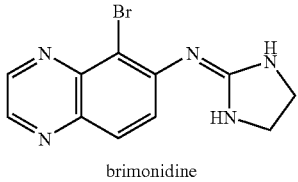
brimonidine

The results of the RSAT assay with several exemplary compounds of the invention are disclosed in Table 1 above together with the chemical formulas of these exemplary compounds. EC$_{50}$ values are nanomolar. NA stands for "not active" at concentrations less than 10 micromolar. IA stands for "intrinsic activity."

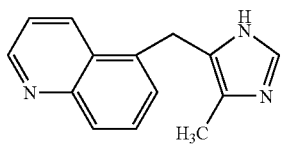
H5

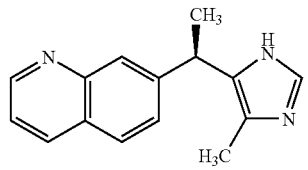
H6

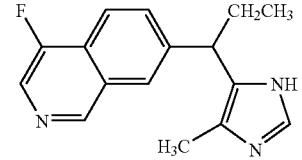
H7

TABLE 1

| Structure | Alpha 1A EC50 (IA) | Alpha 2A EC50 (IA) | Alpha 2B EC50 (IA) | Alpha 2C EC50 (IA) |
|---|---|---|---|---|
| 22 | 116 (1.10) | 284 (0.43) | 16 (1.07) | 268 (0.77) |
| 10 | 540 (1.05) | NA | 76 (0.96) | 521 (0.57) |
| 17 | NA | NA | 30 (0.70) | 3110 (0.32) |
| 5 | 1730 (0.75) | NA | 117 (0.70) | NA |

Compounds 22, 10, 17, and 5 are named as follows:
8-methyl-7-((5-methyl-1H-imidazol-4-yl)methyl)quinoline(1);
7- ((5-methyl-1H-imidazol-4-yl)methyl)quinoline (2);
8- (1-(5-methyl-1H-imidazol-4-yl)ethyl)quinoline (3); and
8-((5-methyl-1H-imidazol-4-yl)methyl)quinoline (4).
Compounds 5-22 are hypothetical examples of compounds that are useful as disclosed herein.

-continued
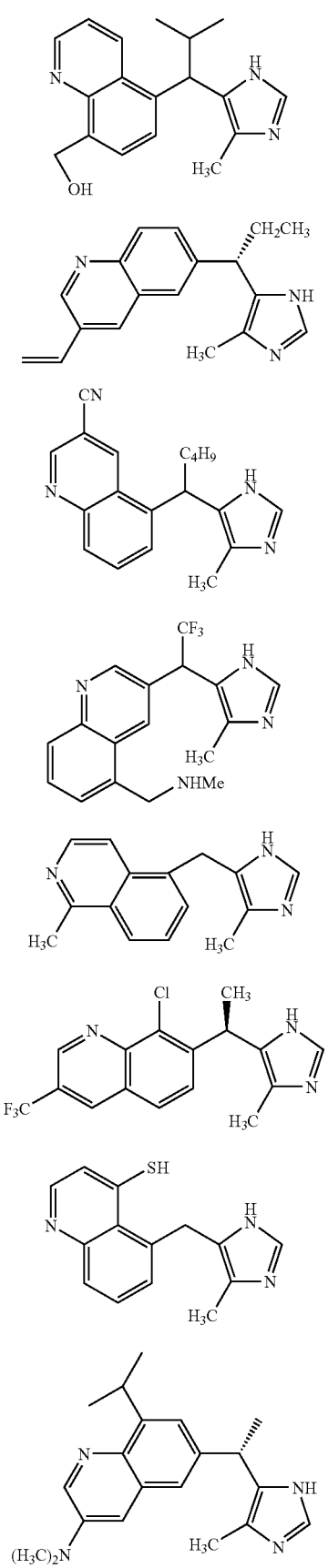
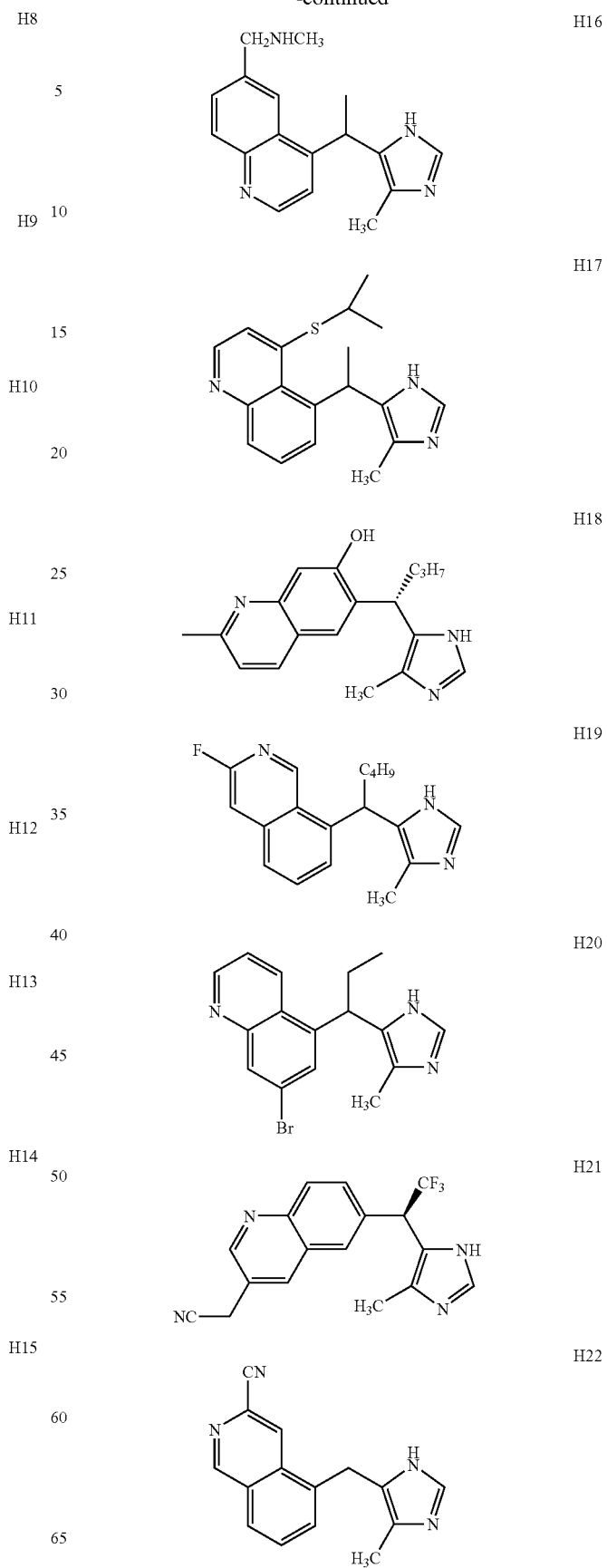

Synthetic Methods

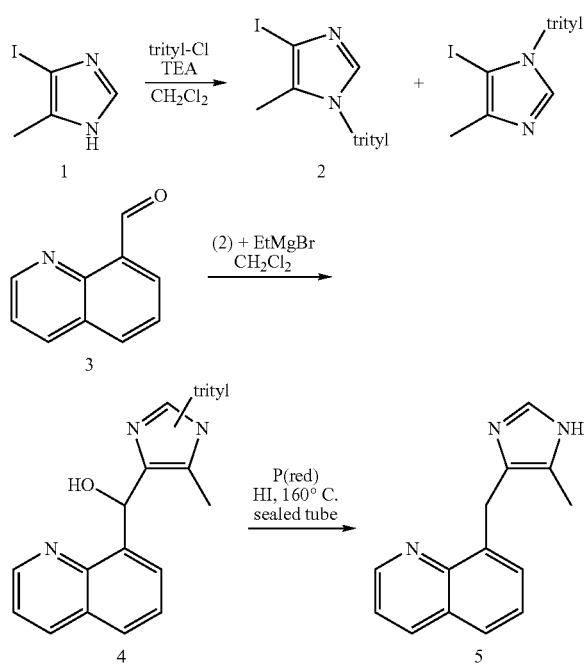

4-Iodo-5-methyl-1-trityl-1H-imidazole and 5-iodo-4-methyl-1-trityl-1H-imidazole (2): A mixture of 4-iodo-5-methyl-1H-imidazole (1) (10.5 g, 50.7 mmol) and trityl chloride (14.4 g, 50.7 mmol) in dichloromethane (100 mL) was added triethyl amine (17.6 mL, 126 mmol). The reaction mixture was stirred at room temperature (room temperature) overnight. The reaction was quenched with ammonium chloride (aq). The aqueous medium was extracted twice with dichloromethane (400 mL). The pooled organic layers were dried over magnesium sulfate. The mixture was filtered, and the solvents were removed under vacuum to give a sticky yellow solid. The crude product was triturated in hexane to give a mixture of 4-iodo-5-methyl-1-trityl-1H-imidazole and 5-iodo-4-methyl-1-trityl-1H-imidazole (2) as a white solid (20 g, 44.4 mmol, 87% yield).

(5-Methyl-1-trityl-1H-imidazol-4-yl)(quinolin-8-yl)methanol and (4-methyl-1-trityl-1H-imidazol-5-yl)(quinolin-8-yl)methanol (4): A solution of (2) (4.79 g, 10.6 mmol) in dichloromethane (70 mL was added ethyl magnesium bromide (3.0 M in diethyl ether, 3.55 mL, 10.6 mmol) dropwise at room temperature. The reaction mixture was stirred for one hour. A solution of quinoline-8-carbaldehyde (3) (1.00 g, 6.37 mmol) in dichloromethane (30 mL) was added dropwise via addition funnel. The reaction mixture was stirred at room temperature overnight. The reaction was quenched with ammonium chloride (aq). The resulting aqueous layer was extracted twice with dichloromethane (300 mL). The pooled organic layers were dried over magnesium sulfate. The mixture was filtered, and the solvents were removed under vacuum. The residue was purified by chromatography on silica gel with 100% ethyl acetate to give (5-methyl-1-trityl-1H-imidazol-4-yl)(quinolin-8-yl)methanol and (4-methyl-1-trityl-1H-imidazol-5-yl)(quinolin-8-yl)methanol (4) as a yellow foamy solid (1.40 g, 2.91 mmol, 46% yield).

8-((5-Methyl-1H-imidazol-4-yl)methyl)quinoline (5): A mixture of (4) (0.71 g, 1.48 mmol) and red phosphorus (0.46 g, 14.18 mmol) in hydroiodic acid (57% in water, 6 mL) was heated in a sealed tube at 160° C. overnight. The reaction mixture was cooled to room temperature, and the sealed tube was slowly opened to release the gas built up inside. The content was poured into crushed ice, and carefully basified with NaOH (aq) to pH>7. The aqueous layer was diluted with chloroform/isopropanol (3:1, 100 mL). The mixture was filtered through a bed of Celite to removed phosphorus. The layers were separated and the aqueous layer was extracted twice with chloroform/isopropanol (3:1, 100 mL). The pooled to organic layers were dried over magnesium sulfate. The mixture was filtered and the solvents were removed under vacuum. The residue was purified by chromatography on silica gel with 2% ammonia saturated methanol in dichloromethane to give 8-((5-methyl-1H-imidazol-4-yl)methyl)quinoline (5) as a light yellow solid (0.23 g, 1.05 mmol, 71% yield). 30 mg of (5) was passed through reverse phase HPLC to give 26.5 mg of an analytically pure sample.

(5)$^1$H NMR (500 MHz, CDCl$_3$): δ 9.00 (dd, J=4.5, 2.0 Hz, 1H), 8.18 (dd, J=8.5, 1.5 Hz, 1H), 7.70 (d, J=8.0 Hz, 1H), 7.58 (d, J=7.0 Hz, 1H), 7.48-7.44 (m, 2H), 7.35 (s, 1H), 4.45 (s, 2H), 2.31 (s, 3H).

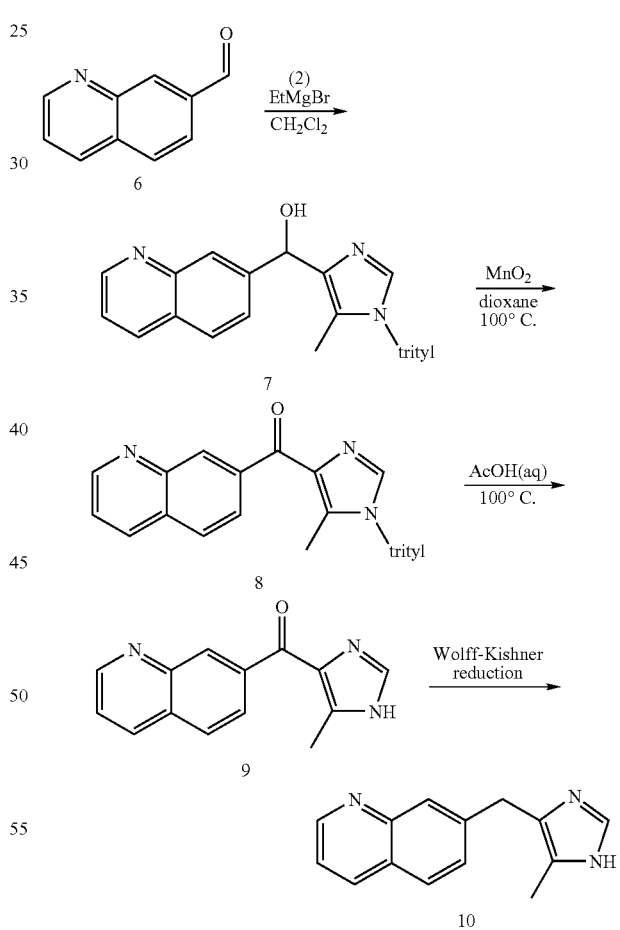

(5-Methyl-1-trityl-1H-imidazol-4-yl)(quinolin-7-yl)methanol and (4-methyl-1-trityl-1H-imidazol-5-yl)(quinolin-7-yl)methanol (7): The same procedure to make (4) was used to prepare compound (7).

(5-Methyl-1-trityl-1H-imidazol-4-yl)(quinolin-7-yl)methanone and (4-methyl-1-trityl-1H-imidazol-5-yl)(quinolin-7-yl)methanone (8): A mixture of (7) (3.45 g, 7.17 mmol), and manganese dioxide (7.33 g, 71.7 mmol) in dioxane (100 mL) was refluxed at 100° C. for 5 h. The reaction mixture was cooled to room temperature. The mixture was filtered through a bed of Celite. The filtrate was evaporated under reduced pressure. The residue was purified by chromatography on silica gel with 60% hexane and 40% ethyl acetate to afford (5-methyl-1-trityl-1H-imidazol-4-yl)(quinolin-7-yl)methanone and (4-methyl-1-trityl-1H-imidazol-5-yl)(quinolin-7-yl)methanone (8), which was carried on to the next step.

(5-Methyl-1H-imidazol-4-yl)(quinolin-7-yl)methanone (9): A solution of (8) in acetic acid/water (12 mL/8 mL) was heated at 110° C. for 1.5 h. The reaction was cooled to room temperature. Crushed ice was added, and basification of reaction with NaOH (s) to pH~6 was followed. The aqueous layer was extracted with chloroform/isopropanol (3:1, 200 mL). The pooled organic layers were dried over magnesium sulfate. The mixture was filtered, and the solvents were removed under vacuum. The residue was purified by chromatography on silica gel with 3% saturated ammonia methanol in dichloromethane to give (5-methyl-1H-imidazol-4-yl)(quinolin-7-yl)methanone (9) as a white solid (0.53 g, 2.24 mmol, 35% over 3 steps).

7-((5-Methyl-1H-imidazol-4-yl)methyl)quinoline (10): A mixture of (9) (0.53 g, 2.23 mmol), potassium hydroxide (0.50 g, 8.91 mol), and hydrazine hydrate (0.45 mL, 14.4 mmol) in ethylene glycol was heated at 120° C. for 1 h, then kept at 165° C. overnight. The reaction mixture was cooled to room temperature and acidified with 2 M HCl (aq) to pH~4. The aqueous layer was washed with chloroform/isoprpanol (3:1, 200 ml). The aqueous layer was basified to pH~7, and extracted with chloroform/isopropanol (3:1, 200 mL). The pooled organic layers were dried over magnesium sulfate. The mixture was filtered, and the solvents were removed under vacuum. The residue was purified by chromatography on silica gel with 3% saturated ammonia methanol in dichloromethane to give 7-((5-methyl-1H-imidazol-4-yl)methyl)quinoline (10) as a yellow foam (0.32 mg, 1.45 mmol, 65% yield).

(10) $^1$H NMR (500 MHz, CDCl$_3$): δ 8.80-8.79 (m, 1H), 8.08 (d, J=7.5 Hz, 1H), 7.78 (s, 1H), 7.68 (d, J=8.0 Hz, 1H), 7.42 (d, J=8.5 Hz, 1H), 7.38 (s, 1H), 7.31 (q, J=4.0 Hz, 1H), 4.07 (s, 2H), 2.17 (s, 3H).

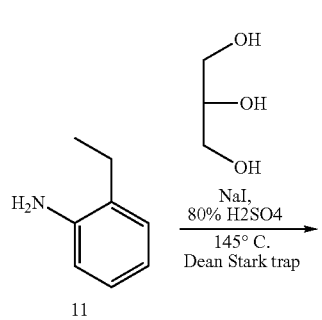

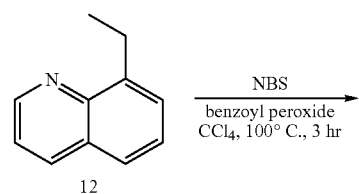

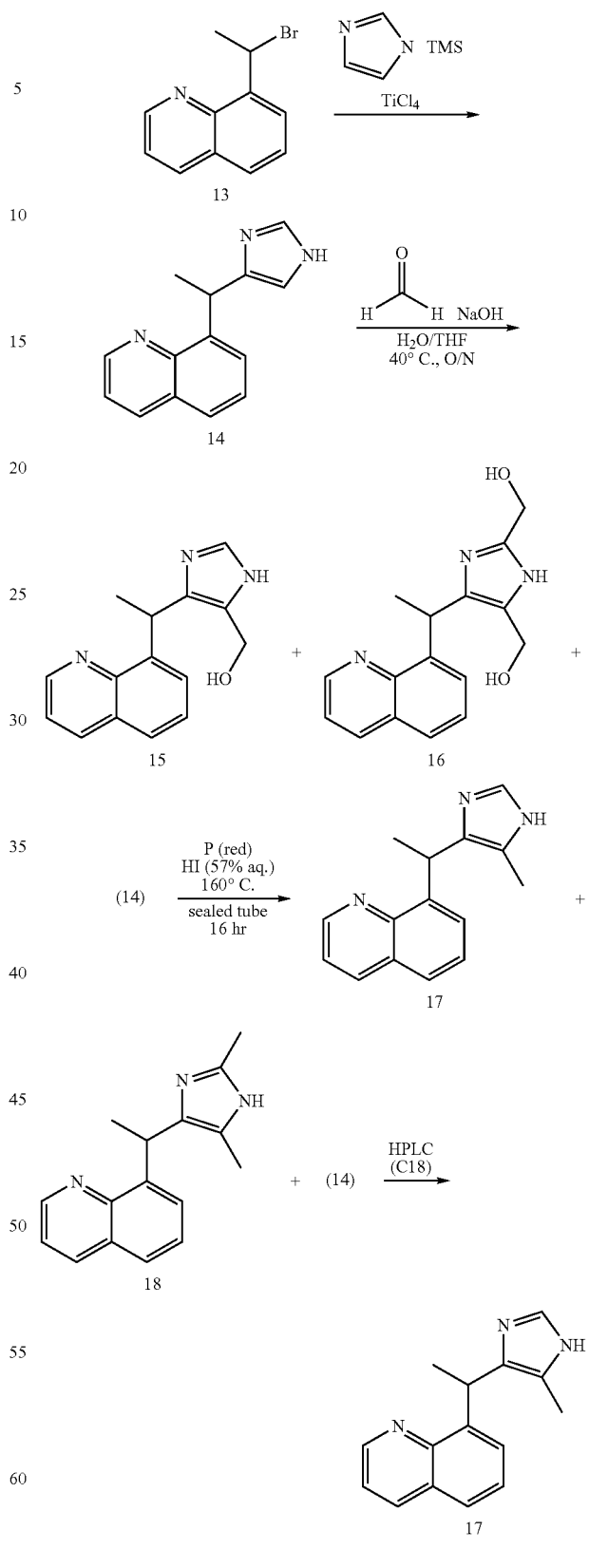

8-Ethylquinoline (12): A mixture of 2-ethylaniline (24.2 g, 200 mmol) and sodium iodide (0.40 g, 2.67 mmol) in 80% sulfuric acid (110 g) at 140° C. was added glycerine (22.0 g, 239 mmol) over a period of 30 m. The reaction mixture was stirred at 140-145° C. for 3 hours in an apparatus fitted with a Dean Stark trap. The reaction mixture was cooled to room temperature. The mixture was neutralized with 25% NaOH (aq) (210 g) to pH 7, and diluted with toluene. The mixture was extracted with ethyl acetate/ether. The pooled organic layers were washed with brine, and dried over magnesium sulfate. The mixture was filtered, to and the solvents were removed under vacuum. The residue was purified by chromatography on silica gel with 5 to 7% ethyl acetate in hexane to give 8-ethylquinoline (12) (24.5 g, 156 mmol, 78% yield).

8-(1-Bromoethyl)quinoline (13): A solution of (12) (3.0 g, 19.1 mmol) in carbon tetrachloride (30 mL) was added NBS (5.10 g, 28.6 mmol), and benzoyl peroxide (0.12 g, 0.48 mmol). The mixture was heated at 100° C. for 3 hours. The reaction was cooled to room temperature. The mixture was filtered through filter paper, and washed with ethyl acetate. The filtrate was adsorbed into silica gel. The mixture was purified by chromatography on silica gel with 5 to 15% ethyl acetate in hexane to give 8-(1-bromoethyl)quinoline (13) (3.5 g, 14.8 mmol, 78% yield).

8-(1-(1H-Imidazol-4-yl)ethyl)quinoline (14): Titanium tetrachloride (3.28 ml, 29.9 mmol) was added to anhydrous chloroform (25 mL) at 0° C. 1-Trimethylsilanyl-1H-imidazole (4.38 ml, 29.9 mmol) in chloroform (25 ml) was added slowly (6 to 7 m) to the TiCl$_4$ solution. The resulting orange solid mixture was stirred at 0° C. for 30 m followed by the addition of (13) (3.53 g, 15.0 mmol) in chloroform (15 mL). The mixture was warmed to room temperature and stirred overnight. The mixture was quenched with water (60 mL). The two layers were separated and the organic layer was extracted twice with water (40 mL). The pooled aqueous layer was neutralized with 4 M NaOH to pH>8. The basic aqueous layer was to extracted with dichloromethane numerous times. The pooled organic layers were washed with brine once, and dried over magnesium sulfate. The mixture was filtered, and the solvent was removed under vacuum. The residue was purified by chromatography on silica gel with 2 to 5% saturated ammonia methanol in dichloromethane to give 8-(1-(1H-imidazol-4-yl)ethyl)quinoline (14) as an off white solid (1.61 g, 7.22 mmol, 48% yield.)

(4-(1-(Quinolin-8-yl)ethyl)-1H-imidazol-5-yl)methanol (15): A solution of (14) (0.41 g, 1.84 mmol) in THF/H$_2$O (4 mL/2 mL) was added 2 N NaOH (1.90 mL, 3.80 mmol), and formaldehyde (aq) (37%, 0.14 mL, 1.88 mmol). The reaction mixture was stirred at 40° C. overnight. TLC and mass spectrometry analyses showed starting material (14), (4-(1-(quinolin-8-yl)ethyl)-1H-imidazol-5-yl)methanol (15), and (4-(1-(quinolin-8-yl)ethyl)-1H-imidazole-2,5-diyl)dimethanol (16). The solvent was evaporated under reduce pressure and the residue was carried on to the next step without further purification.

8-(1-(5-Methyl-1H-imidazol-4-yl)ethyl)quinoline (17): The same synthetic method to make (5) was used. The crude product consisted of (14), 8-(1-(5-methyl-1H-imidazol-4-yl)ethyl)quinoline (17), and 8-(1-(2,5-dimethyl-1H-imidazol-4-yl)ethyl)quinoline (18). The mixture was purified by reverse phase HPLC to give (17) as a solid (0.077 g, 0.32 mmol, 18% over 2 steps).

(17) $^1$H NMR (500 MHz, CDCl$_3$): δ 8.96 (dd, J=4.5, 2.0, 1H), 8.14 (dd, J=8.5, 1.5 Hz, 1H), 7.65 (d, J=7.5 Hz, 1H), 7.46-7.38 (m, 2H), 7.41 (s, 1H), 5.23 (bs, 1H), 2.22 (s, 3H), 1.81 (d, J=7.5 Hz, 3H).

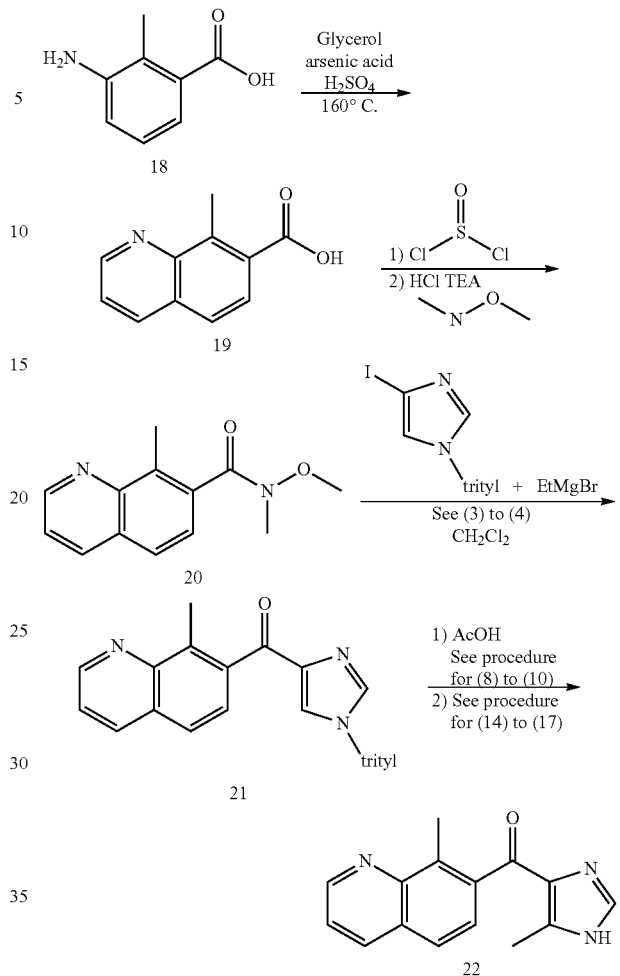

8-Methylquinoline-7-carboxylic acid (19): A mixture of 3-amino-2-methylbenzoic acid (18) (6.1 g, 39.7 mmol), arsenic acid (7.4 g, 52.3 mmol), and glycerol (5.8 mL, 79.4 mmol) in sulfuric acid (9 mL) was heated at 160° C. for 5 hours. The reaction mixture was cooled to room temperature and diluted with water. The mixture was filtered through a bed of celite and the filtrate was adjusted with 2 M NaOH to pH~6. The aqueous layer was extracted numerous times with chloroform/isopropanol. The pooled organic layers were removed under vacuum. The solid residue was triturated with chloroform. The mixture was to filtered, and the solid was washed with hexane and dried under high vacuum to give 8-methylquinoline-7-carboxylic acid (19) 3.86 g (20.6 mmol, 52% yield).

N-Methoxy-N,8-dimethylquinoline-7-carboxamide (20): (19) (3.86 g, 20.6 mmol) was refluxed in thionyl chloride (15 mL, 204 mmol) for one hour. The reaction mixture was cooled to room temperature and the thionyl chloride was removed under vacuum. The residue was diluted with dichloromethane and the solvent was removed under vacuum. The solid residue was solvated with dichloromethane (120 mL), N,O-dimethylhydroxylamine hydrochloride (3.0 g, 30.1 mmol), and triethylamine (10.6 mL, 76.0 mmol) at 0° C., and the mixture was stirred for several hours. The reaction mixture was quenched with water, and extracted with dichloromethane. The pooled organic layers were dried over magnesium sulfate. The mixture was filtered, and the solvents were removed under vacuum to give the crude product as an oil. The oil was purified by chromatography on silica gel with 50% hexane:ethyl acetate to 40% hexane:ethyl acetate to give N-methoxy-N,8-dimethylquinoline-7-carboxamide (20) as a yellow oil (3.9 g, 17.0 mmol, 82% yield).

(8-Methylquinolin-7-yl)(1-trityl-1H-imidazol-4-yl) methanone (21) was synthesized from (20) and 4-iodo-1-trityl-1H-imidazole via the procedure used in the preparation of (4) from (3) above.

8-Methyl-7-((5-methyl-1H-imidazol-4-yl)methyl)quinoline (22): (21) was subjected to the conditions above for steps 8 to 10, and 14 to 17 to yield (22).

8-Methyl-7-((5-methyl-1H-imidazol-4-yl)methyl)quinoline (22): $^1$H NMR (500 MHz, CD$_3$OD): δ 8.84 (dd, J=4.5, 1.5 Hz, 1H), 8.23 (dd, J=8.5, 1.5 Hz, 1H), 7.67 (d, J=8.0 Hz, 1H), 7.49 (s, 1H), 7.44 (dd, J=8.5, 2.0 Hz, 1H), 7.34 (d, J=8.0 Hz, 1H), 4.15 (s, 2H), 2.79 to (s, 3H), 2.14 (s, 3H).

Additional substitution on the quinolinyl ring of A may be obtained by purchasing the corresponding substituted quinolinecarbaldehyde, e.g. substituted versions of 3 or 6; or by purchasing substituted anilines, e.g. substituted versions of 11 or 18. Alternatively, additional substituents may be added to the quinolinyl ring by methods known in the art.

Different R groups may be obtained by using the appropriate analog of 11 or treating 21 or an analog with RMgBr or an equivalent reagent.

Other alternate routes to a wide variety of compounds are readily apparent to those skilled in the art.

These compounds will be useful for the treatment of mammals, including humans, with a range of conditions and diseases that include, but are not limited to, ischemic neuropathies, optic neuropathy, neuropathic pain, visceral pain, corneal pain, headache pain, migraine, cancer pain, back pain, irritable bowel syndrome pain, muscle pain and pain associated with diabetic neuropathy, the treatment of diabetic retinopathy, other retinal degenerative conditions, cognitive deficits, neuropsychiatric conditions, drug dependence and addiction, withdrawal symptoms, spasticity, autism, Huntington's disease, attention deficit disorder, attention deficit hyperactivity disorder ADHD, obsessive-compulsive disorders, Tourette's disorder, Parkinson's ALS, and other motor or movement disorders and diseases.

Other uses include dilation of the pupil, increase blood pressure, treating nasal congestion, and vasoconstriction in ocular tissue.

These compounds may be formulated into solid, liquid, or other types of dosage forms using methods known in the art. Both formulation of dosage forms and determination of a therapeutically effective dose can be readily made by a person of ordinary skill using routine methods.

The foregoing description details specific methods and compositions that can be employed to practice the present invention, and represents the best mode contemplated. However, it is apparent for one of ordinary skill in the art that further compounds with the desired pharmacological properties can be prepared in an analogous manner, and that the disclosed compounds can also be obtained from different starting compounds via different chemical reactions. Similarly, different pharmaceutical compositions may be prepared and used with substantially the same result. Thus, however detailed the foregoing may appear in text, it should not be construed as limiting the overall scope hereof; rather, the ambit of the present invention is to be governed only by the lawful construction of the claims.

What is claimed is:

1. A compound of the formula

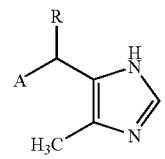

wherein R is H, C$_{1-4}$ alkyl, or CF$_3$;

A is quinolinyl having 0, 1, 2, or 3 substituents selected from CH$_3$, ethyl, t-butyl, ethenyl, ethynyl, OCH$_3$, NHMe, NMe$_2$, Br, Cl, F, phenyl, and combinations thereof.

2. The compound of claim 1 wherein R is H.

3. The compound of claim 1 wherein A is unsubstituted.

4. The compound of claim 1 having the formula

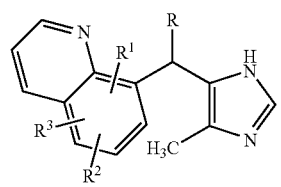

wherein R$^1$, R$^2$, and R$^3$ are independently hydrogen or substituents selected from CH$_3$, ethyl, t-butyl, ethenyl, ethynyl, OCH$_3$, NHMe, NMe$_2$, Br, Cl, F, phenyl, and combinations thereof.

5. The compound of claim 4 having the formula

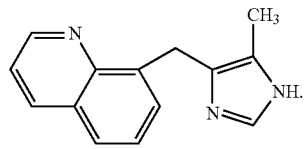

6. The compound of claim 1 having the formula

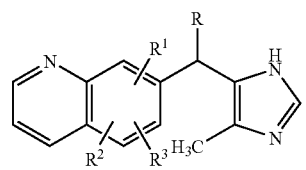

wherein R$^1$, R$^2$, and R$^3$ are independently hydrogen or substituents selected from CH$_3$, ethyl, t-butyl, ethenyl, ethynyl, OCH$_3$, NHMe, NMe$_2$, Br, Cl, F, phenyl, and combinations thereof.

7. The compound of claim 6 having the formula

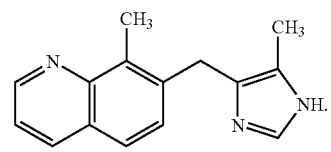

8. The compound of claim 1 selected from:
8-methyl-7-((5-methyl-1H-imidazol-4-yl)methyl)quinoline;
7-((5-methyl-1H-imidazol-4-yl)methyl)quinoline;
8-(1-(5-methyl-1H-imidazol-4-yl)ethyl)quinolin; and
8-((5-methyl-1H-imidazol-4-yl)methyl)quinoline.

9. The compound according to any one of claims 1, 4, and 6 wherein R is methyl.

10. The compound according to any one of claims 1, 4, and 6 wherein R is ethyl.

11. The compound according to any one of claims 1, 4, and 6 wherein R is $CF_3$.

12. The compound of claim 6 having the formula

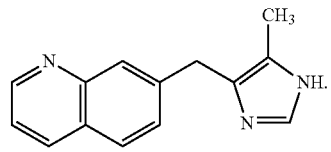

* * * * *